US012789008B2

(12) United States Patent
Nioutsikou et al.

(10) Patent No.: US 12,789,008 B2
(45) Date of Patent: Nov. 10, 2026

(54) SYSTEM FOR SUPPORTING A BRACHYTHERAPY TREATMENT, METHOD FOR PROVIDING A SUPERVISION INFORMATION AND COMPUTER PROGRAM PRODUCT

(71) Applicant: Siemens Medical Solutions USA, Inc., Malvern, PA (US)

(72) Inventors: Elena Nioutsikou, Erlangen (DE); Antonis Kalemis, Uttenreuth (DE)

(73) Assignee: SIEMENS MEDICAL SOLUTIONS USA, INC., Malvern, PA (US)

( * ) Notice: Subject to any disclaimer, the term of this patent is extended or adjusted under 35 U.S.C. 154(b) by 1233 days.

(21) Appl. No.: 17/691,093

(22) Filed: Mar. 9, 2022

(65) Prior Publication Data

US 2022/0288417 A1 Sep. 15, 2022

(30) Foreign Application Priority Data

Mar. 10, 2021 (DE) ..................... 10 2021 202 348.7

(51) Int. Cl.
*A61N 5/10* (2006.01)

(52) U.S. Cl.
CPC ......... *A61N 5/1027* (2013.01); *A61N 5/1007* (2013.01)

(58) Field of Classification Search
CPC .. A61N 5/1001; A61N 5/1002; A61N 5/1007; A61N 5/1014–1017;
(Continued)

(56) References Cited

U.S. PATENT DOCUMENTS

2010/0312038 A1* 12/2010 Shechter .............. A61N 5/1015 600/3
2013/0289332 A1* 10/2013 Purdie .................. A61N 5/1039 600/1
(Continued)

FOREIGN PATENT DOCUMENTS

| | | | |
|---|---|---|---|
| EP | 2595535 | B1 | 2/2019 |
| EP | 3432984 | B1 | 7/2019 |
| WO | 2015028641 | A1 | 3/2015 |

OTHER PUBLICATIONS

ICRP, "Prevention of high-dose-rate brachytherapy accidents", ICRP publication 97. Ann ICRP, 35:1-51, 2005. pp. 1-9.
(Continued)

*Primary Examiner* — Carrie R Dorna
(74) *Attorney, Agent, or Firm* — Lempia Summerfield Katz LLC

(57) ABSTRACT

A system for supporting a brachytherapy treatment includes a medical imaging system and a processing unit. The medical imaging system includes a SPECT unit and/or a CT unit. The processing unit is configured to receive a planning dataset, and determine a brachytherapy treatment plan based on the planning dataset. The treatment plan includes a planned dose distribution for a radiation source. The medical imaging system is configured to acquire a supervision dataset that includes an intra-procedural representation of the radiation source that, in an operating state of the system, has been positioned at a treatment site within a treatment region via a medical guide instrument. The processing unit is configured to register the supervision dataset and the planning dataset, determine an actual dose distribution based on the supervision dataset, and provide supervision information based on a comparison between the planned and actual dose distribution.

18 Claims, 7 Drawing Sheets

(58) Field of Classification Search
CPC .... A61N 5/1027; A61N 5/103; A61N 5/1071; A61N 2005/1008; A61N 2005/1011; A61N 2005/1012; A61N 2005/1018; A61N 2005/1024
See application file for complete search history.

(56) References Cited

U.S. PATENT DOCUMENTS

| | | | | |
|---|---|---|---|---|
| 2013/0303902 | A1 | 11/2013 | Smith et al. | |
| 2014/0275713 | A1* | 9/2014 | Bask | A61N 5/1001 600/3 |
| 2016/0184611 | A1 | 6/2016 | Brosens-Kessels et al. | |
| 2016/0375270 | A1 | 12/2016 | Todor et al. | |
| 2019/0046814 | A1* | 2/2019 | Senden | A61B 34/10 |

OTHER PUBLICATIONS

Rivard, Mark J., et al. "Update of AAPM Task Group No. 43 Report: A revised AAPM protocol for brachytherapy dose calculations." Medical physics 31.3 (2004): 633-674.
Smith, Ryan L., et al. "An integrated system for clinical treatment verification of HDR prostate brachytherapy combining source tracking with pretreatment imaging." Brachytherapy 17.1 (2018): 111-121.
Van Audenhaege, Karen, et al. "Review of SPECT collimator selection, optimization, and fabrication for clinical and preclinical imaging." Medical physics 42.8 (2015): 4796-4813.
Zhang et al. "Dose Distribution Detected by SPECT/CT in a Patient with Prostate Cancer Treated with 125I Seeds: A Case Report", in Proceedings of the American Brachytherapy Society, vol. 15, Suppl. 1, S183-S184 Abstract, May 1, 2016.

* cited by examiner

SYSTEM FOR SUPPORTING A BRACHYTHERAPY TREATMENT, METHOD FOR PROVIDING A SUPERVISION INFORMATION AND COMPUTER PROGRAM PRODUCT

This application claims the benefit of German Patent Application No. DE 10 2021 202 348.7, filed on Mar. 10, 2021, which is hereby incorporated by reference in its entirety.

BACKGROUND

The present embodiments relate to a system for supporting a brachytherapy treatment, a method for providing a supervision information, and a computer program product.

For a brachytherapy treatment, often times medical guide instruments are inserted into a body of a subject (e.g., a patient), such that a distal end portion (e.g., a tip) of each medical guide instruments is located adjacent or within an anatomical region of the treatment region. The medical guide instruments (e.g., the distal end portions and/or tips of the medical guide instruments) are frequently denoted as applicators. The medical guide instruments may, for example, be inserted and/or positioned within the treatment region under ultra-sound monitoring. Commonly, a brachytherapy treatment plan (e.g., based on medical images of the treatment region after the medical guide instruments have been positioned) that specifies dwell positions and/or dwell times for a radiation source within the medical guide instruments is created. The medical guide instruments may further be connected to an afterloader unit that may include a stepping motor for introducing and translating the radiation source inside the medical guide instruments. The afterloader unit may be configured to receive the brachytherapy treatment plan and to control the stepping motor accordingly. The afterloader unit may further be configured to remove and/or reposition the radiation source to the next dwell position after expiry of the respective dwell time. In addition, the afterloader unit often includes multiple "channels", where the afterloader unit may be configured to introduce and/or translate the at least one radiation source in the medical guide instruments through these "channels" (e.g., simultaneously or sequentially). Thereby, the medical guide instruments may be positioned at different locations relative to the tissue to be treated (e.g., a tumor) in order to achieve an optimal radiation treatment.

There are different variants of brachytherapy (e.g., a high-dose rate brachytherapy (HDR brachytherapy) and/or a pulsed dose rate brachytherapy (PDR brachytherapy)). The aforementioned variants of brachytherapy often include delivering very high doses with high gradients within a few treatment fractions (e.g., to treat solid tumors). A precise positioning of the at least one radiation source is essential for an accurate dose delivery. By way of example, as has been reported by Rivard et al. in "Update of AAPM Task Group No. 43 Report: A revised AAPM protocol for brachytherapy dose calculations," Med. Phys. 31:633-674, 2004, a 1 mm uncertainty may result in a 20% shift in dose at 10 mm from the at least one radiation source for a typical Iridium-192 ($^{192}$Ir) source. Further, it is known from Smith et al., "An integrated system for clinical treatment verification of HDR prostate brachytherapy combining source tracking with pre-treatment imaging," Brachytherapy 17: 111-121, 2018, that deviations from the treatment plan may have a significant clinical impact (e.g., due to the high doses often delivered within seconds and due to the lack of remedies for radiation damage). In 2005, the International Commission on Radiological Protection (ICRP) published an investigation that showed that a significant share of radiation events is often caused by human errors related to manual procedures.

HDR and/or PDR brachytherapy may be delivered with a variety of medical guide instruments (e.g., interstitial needles and/or intracavity applicators and/or tubes and/or catheters).

The medical guide instruments may be extracted after completion of the HDR and/or PDR brachytherapy treatment. Without treatment verification and/or supervision during a brachytherapy treatment, a number of errors may potentially arise. For example, patient motion and/or patient relocation between rooms may cause a shift of one or more medical guide instruments (e.g., between a time of planning and a time of treatment delivery. As another example, organ filling between the time of planning and the time of treatment delivery may cause a deviation between planned and delivered dose. As yet another example, a wrong identification of the tip of the medical guide instrument, at which the at least one radiation source is often times initially positioned before translating along its path, may occur. This type of error is particularly frequent in cases where magnetic resonance imaging (MRI) is used for treatment planning. As another example, a wrong identification of the medical guide instruments (e.g., when medical guide instruments are crossing and depth information is lacking) may occur. In such case, a systematic error may arise, which may potentially carry forward to the rest of the treatment procedure, including dosimetry planning and/or treatment delivery. If one or more channels of the afterloader unit are wrongly connected to the respective medical guide instruments, a wrong delivery of the treatment plan may occur.

For example, the document by Zhang et al., "Dose Distribution Detected by SPECT/CT in a Patient with Prostate Cancer Treated with 125I Seeds: A Case Report," in Proceedings of the American Brachytherapy Society, Vol. 15, Suppl. 1, S183-S184, May 1, 2016, discloses a method to scan a pelvic cavity of a prostate cancer patient treated with Iodine-125 ($^{125}$I) seed implantation by using low-dose high-resolution SPECT/CT.

In today's clinical workflows, real-time treatment verification in brachytherapy does not frequently occur. Hence, most brachytherapy treatments are delivered in a "blind" fashion by connecting the various channels of the afterloader unit to the medical guide instruments, which are inserted into the subject, and starting the treatment.

In order to address these problems, a number of methods have been proposed. For example, in-vivo dosimetry may be conducted with point detectors that may be inserted in locations close to path of the radiation source. Adversely, such methods are invasive, and the location of the point detectors is often restricted to natural cavities of the subject and/or an outer surface of the subject (e.g., a skin section). Thereby, dose measurements are often limited to one or more points.

As another example, electromagnetic tracking (EMT) may be used for tracking the at least one radiation source with high spatial resolution. However, the intrinsically different coordinate systems of the EMT and a medical imaging system used for creating the treatment plan (e.g., for contouring an anatomy of interest and/or dose calculations) may be problematic. Hence, EMT cannot track the at least one radiation source in relation to the subject's anatomy.

Similar problems may arise when tracking the at least one radiation source using flat panel detectors (FPD). Often times, a coordinate system of the FPD cannot be correlated to the coordinate system of the medical imaging system used for treatment planning. Hence, no in-vivo dosimetry may be established. In addition, the delivered dose distribution may often only be recalculated post-treatment. However, by doing so, there is no ability for medical staff to intervene and/or interrupt the brachytherapy treatment if required.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a real-time brachytherapy treatment supervision and/or verification is provided.

In a first aspect, the present embodiments include a system for supporting a brachytherapy treatment. The system includes a medical imaging system and a processing unit. Further, the medical imaging system includes a single photon emission computed tomography (SPECT) unit and/or a computed tomography (CT) unit. In addition, the processing unit is configured to receive a planning dataset including a pre-procedural representation of a treatment region of a subject. The subject may be a human patient and/or animal patient and/or a phantom. Further, the processing unit is configured to determine a brachytherapy treatment plan based on the planning dataset, where the brachytherapy treatment plan includes a planned dose distribution for at least one radiation source (e.g., a plurality of radiation sources) to be positioned within the treatment region. Further, the medical imaging system is configured to acquire a supervision dataset. The supervision dataset includes an intra-procedural representation of the at least one radiation source that, in an operating state of the system, has been positioned at a treatment site within the treatment region via at least one medical guide instrument (e.g., multiple medical guide instruments). In addition, the processing unit is configured to register the supervision dataset and the planning dataset. Further, the processing unit is configured to determine an actual dose distribution based on the supervision dataset. Further, the processing unit is configured to provide a supervision information based on a comparison between the planned and actual dose distribution.

The processing unit may include an interface that may be configured to receive the planning dataset (e.g., via a wired and/or wireless transmission). For example, the processing unit may be configured to receive the planning dataset via collecting and/or reading out data from an electronically readable storage medium and/or via receiving data from a memory unit (e.g., a database) and/or from the medical imaging system (e.g., the CT unit). Alternatively, the planning dataset may be provided by a different medical imaging system (e.g., a magnetic resonance imaging system (MRI) and/or a positron emission tomography system (PET) and/or an ultra-sound system and/or an X-ray system).

The planning dataset may include a pre-procedural representation (e.g., image data) of the treatment region of the subject. Further, the treatment region may include an anatomical region of the subject (e.g., an organ and/or tissue). Further, the treatment region (e.g., the anatomical region) may include a tumor and/or tumorous tissue that is to be treated via the brachytherapy treatment in the operating state of the system. In one embodiment, the planning dataset may feature a two-dimensional (2D) and/or three-dimensional (3D) spatial resolution. In addition, the planning dataset may be time-resolved. Further, the planning dataset (e.g., the pre-procedural representation of the treatment region) may represent (e.g., map) the treatment region pre-procedurally (e.g., at a time before the at least one medical guide instrument and/or the at least one radiation source have been positioned within the treatment region). The planning dataset may further be registered with a coordinate system of the subject. Further, the planning dataset may include a contrasted and/or segmented region of interest (ROI) (e.g., a tumor and/or tumorous tissue) to be treated via brachytherapy. In addition, the planning dataset may include a further segmented region (e.g., an anatomical region) that is to be spared from radiation during brachytherapy.

The brachytherapy treatment plan may include a planned dose distribution for the at least one radiation source (e.g., a plurality of radiation sources) to be positioned (e.g., temporarily) within the treatment region. The planned dose distribution may be 2D and/or 3D spatially resolved and/or time-resolved. Thereby, the planned dose distribution may include a map of an overall radiation to be deposited by the at least one radiation source during execution of the brachytherapy treatment plan. The brachytherapy treatment plan (e.g., the planned dose distribution) may be registered with the planning dataset and/or a coordinate system of the subject.

In addition, the brachytherapy treatment plan may include at least one planned dwell position and at least one planned dwell time (e.g., multiple dwell positions and multiple dwell times) for the at least one radiation source to be positioned (e.g., temporarily). In one embodiment, the brachytherapy treatment plan may include at least one planned dwell time for each planned dwell position. Via accumulation of the radiation deposited by the at least one radiation source at the at least one planned dwell position and for a duration of the at least one planned dwell time, the planned dose distribution may be achieved.

In one embodiment, the brachytherapy treatment plan may include the planned dose distribution according to an HDR brachytherapy and/or a PDR brachytherapy treatment. Further, the at least one radiation source may include a radionuclide that is configured to emit gamma photons (e.g., high-energy gamma photons at 100 keV or above).

The medical imaging system may include a single-photon emission computed tomography (SPECT) system and/or a computed tomography (CT) system. In one embodiment, the medical imaging system may include a SPECT/CT system (e.g., a hybrid imaging system) including a SPECT unit and a CT unit.

The SPECT unit may include at least one detection (e.g., two detection units). Each of the at least one detection unit includes a gamma camera. Further, the gamma camera may be configured to detect gamma photons emitted by the at least one radiation source. The at least one detection unit may further be configured to map the detected gamma photons (e.g., via a projection mapping). In one embodiment, the at least one detection unit may be mounted rotatably around an axis of rotation and thereby be enabled to map the detected gamma photons tomographically.

The CT unit may include an X-ray source and an X-ray detector (e.g., a row detector and/or a multi-row detector). The X-ray source and the X-ray detector may be mounted on a common rotating gantry frame opposite each other in relation to an axis of rotation. The rotating gantry frame may further be mounted rotatably around the axis of rotation. The X-ray source may be configured to emit an X-ray bundle (e.g., a fan-beam) towards the oppositely mounted X-ray detector. After an interaction between the X-ray bundle and the subject, the X-ray detector may be configured to receive a transmitted portion of the X-ray bundle.

The subject may be positioned within a patient receiving section of the medical imaging system (e.g., with a longitudinal axis of the subject substantially aligned in parallel to the axis of rotation of the SPECT unit and/or the CT unit). Further, the medical imaging system (e.g., the SPECT unit and/or the CT unit) may be configured to acquire the supervision dataset of the subject.

The supervision dataset may include an intra-procedural representation (e.g., image data and/or dosimetric data) of the at least one radiation source that, in the operating state of the system, has been positioned at the treatment site (e.g., temporarily at a dwell position) within the treatment region of the subject. In one embodiment, the supervision dataset may feature a 2D and/or 3D spatial resolution. In addition, the supervision dataset may be time-resolved. Further, the supervision dataset (e.g., the intra-procedural representation of the at least one radiation source) may represent (e.g., map) the at least one radiation source at the treatment site intra-procedurally (e.g., at a time when the at least one medical guide instrument and the at least one radiation source have been positioned within the treatment region). In one embodiment, the supervision dataset may include a dosimetric mapping of the radiation (e.g., gamma photons) emitted by the at least one radiation source (e.g., 2D and/or 3D spatially resolved and/or time-resolved). If, in the operating state of the system, a plurality of similar or different radiation sources has been positioned at the treatment site within the treatment region, the supervision dataset may include an intra-procedural representation of the plurality of radiation sources.

The processing unit may be further configured to register the supervision dataset and the planning dataset. The registration may be based on geometrical and/or anatomical features that are commonly mapped in the planning dataset and the supervision dataset (e.g., a contour and/or marker structure and/or anatomical landmarks and/or contrast values). Further, the registration may be based on acquisition parameters of the medical imaging system for the acquisition of the planning dataset and/or the supervision dataset. In addition, the registration may be based on positioning information (e.g., relative and/or absolute positioning information) with regard to the subject. The registration may include a rigid and/or non-rigid transformation of the planning dataset and/or the supervision dataset. For example, the registration between the supervision dataset and the planning dataset may include a 2D-2D-registration, a 2D-3D-registration, or a 3D-3D-registration.

The processing unit may further be configured to determine an actual dose distribution based on the supervision dataset. For example, the processing unit may be configured to determine the actual dose distribution based on the amount (e.g., incidence) of gamma photons that were emitted by the at least one radiation source mapped in the supervision dataset. Alternatively or in addition, the processing unit may be configured to receive information about the at least one radioactive source (e.g., a size and/or decay information, such as a decay activity and/or a decay energy). Further, the processing unit may be configured to determine the actual dose distribution based on a trajectory of the at least one radiation source in the treatment region (e.g., at least one actual dwell position and at least one actual dwell time). The processing unit may be configured to identify the trajectory based on the supervision dataset. Further, the determination of the actual dose distribution may include a combination (e.g., a multiplication and/or integration and/or convolution) of the at least one actual dwell position, the at least one actual dwell time, and a radioactivity parameter of the at least one radiation source.

The processing unit may further be configured to provide the supervision information based on the comparison between the planned and actual dose distribution. For example, the processing unit may be configured to globally and/or locally compare the planned and actual dose distribution. In one embodiment, the supervision information may include information about a deviation (e.g., global and/or local deviation) between the planned dose distribution and the actual dose distribution. For example, the supervision information may include a qualitative information about an occurrence of the deviation between the planned and actual dose distribution. For example, the supervision information may include qualitative information if the deviation between the planned and actual dose distribution exceeds a pre-defined threshold. Further, the supervision information may include quantitative information about the deviation between the planned and actual dose distribution. In one embodiment, the supervision information (e.g., the quantitative and/or qualitative information about the deviation between the planned dose distribution and the actual dose distribution) may be 2D and/or 3D spatially resolved and/or time-resolved. By way of example, the supervision information may be configured as a signal and/or a deviation map and/or an overlay of a visualization of the planned and actual dose distribution. Further, the processing unit may be configured to provide the supervision information including a workflow hint and/or a control signal. The workflow hint may include at least one suggestion for reducing and/or limiting the deviation between the planned dose distribution and the actual dose distribution. Further, the control signal may include a command for controlling the afterloader unit (e.g., for repositioning and/or retracting the at least one radiation source).

The providing of the supervision information may include a storing on an electronically readable storage medium and/or a displaying on a display unit and/or a transmitting to a further processing unit and/or transmitting to the afterloader unit. In one embodiment, the system may be configured to repeatedly acquire the supervision dataset and to update the actual dose distribution. In addition, the processing unit may be configured to repeatedly determine the actual dose distribution and to provide the supervision information based on the comparison between the updated actual dose distribution and the planned dose distribution. Thereby, the system of one or more of the present embodiments may provide for a brachytherapy treatment supervision (e.g., a real-time monitoring). Further, the provided supervision information may provide a real-time feedback to medical staff controlling the system.

In an embodiment of the system, the brachytherapy treatment plan may include at least one planned dwell position and at least one planned dwell time for the at least one radiation source to be positioned. For example, the brachytherapy treatment plan may include at least one planned dwell time for each planned dwell position. Further, the intra-procedural representation of the at least one radiation source, which is comprised in the supervision dataset, may be time-resolved. The processing unit may further be configured to determine at least one actual dwell position and at least one actual dwell time of the at least one radiation source based on the supervision dataset. Further, the comparison between the planned dose distribution and the actual dose distribution may include a comparison between the at least one planned dwell position and the at least one actual dwell position and between the at least one planned dwell time and the at least one actual dwell time.

In one embodiment, the supervision dataset may include pixels and/or voxels representing the treatment region intra-procedurally. The intra-procedural representation of the at least one radiation source may be identified (e.g., localized) in the supervision dataset (e.g., in the coordinate system of the subject). In one embodiment, the processing unit may be configured to determine the at least one actual dwell position and at least one actual dwell time based on the supervision dataset. The identification of the intra-procedural representation of the at least one radiation source in the supervision dataset may include an identification (e.g., a segmentation) of pixels and/or voxels of the supervision dataset; the pixels and/or voxels represent the at least one radiation source. If the supervision dataset includes intra-procedural dosimetric data of the at least one radiation source (e.g., a mapping of an incidence of gamma photons), the pixels and/or voxels representing the at least one radiation source may be identified by comparing their values (e.g., an incidence value and/or a radiation dose value) with a dosimetric threshold. Thereby, pixels and/or voxels in the supervision dataset with a value equal or above the dosimetric threshold may be identified as representing the at least one radiation source. If the supervision dataset includes intra-procedural image data of the treatment region, the intra-procedural representation of the at least one radiation source may be identified as a saturated and/or bright region within the representation of the treatment region. The pixels and/or voxels representing the at least one radiation source may be identified by comparing their values (e.g., an intensity and/or absorption and/or attenuation and/or contrast value) with a first image value threshold. The processing unit may further be configured to associate each pixel and/or voxel of the supervision dataset with a spatial position (e.g., in a coordinate system of the subject). Thereby, the processing unit may be configured to determine the at least one actual dwell position and at least one actual dwell time of the at least one radiation source based on the supervision dataset. If, in the operating state of the system, multiple radiation sources have been positioned at the treatment site within the treatment region, the processing unit may be configured to determine at least one actual dwell position and at least one actual dwell time for each of the multiple radiation sources.

Further, the comparison between the planned dose distribution and the actual dose distribution may include a comparison between the at least one planned dwell position and the at least one actual dwell position and between the at least one planned dwell time and the at least one actual dwell time. Thereby, the system may be configured to validate a correct execution of the brachytherapy treatment plan.

In an embodiment of the system, the SPECT unit may include a first detection unit. Further, the first detection unit may include a first gamma camera and a first collimator. The first collimator may be spatially arranged within a field of view of the first gamma camera. Further, the first collimator may be configured to collimate incident gamma photons towards the first gamma camera. In addition, the first gamma camera may be configured to detect gamma photons emitted by the at least one radiation source. Further, the SPECT unit may be configured to acquire the supervision dataset by mapping the detected gamma photons.

The first gamma camera may include a crystal layer (e.g., a thallium doped sodium iodide (NaI) crystal layer, such as a ⅝" or a ⅜" NaI crystal layer) that may be in optical contact with an array of photomultiplier tubes. The crystal layer may be configured to absorb gamma photons and emit fluorescent light in response. Further, the array of photomultiplier tubes may be configured to detect the fluorescent light. Thereby, the first gamma camera may be configured to count and/or spatially map an incidence of gamma photons. For example, the first gamma camera may be configured to detect gamma photons emitted by the at least one radiation source.

The field of view of the first gamma camera may denote a spatial detection range where the first gamma camera (e.g., the crystal layer) is sensitive to gamma photons. In one embodiment, the first collimator may be spatially arranged (e.g., mounted) within the field of view of the first gamma camera (e.g., adjacent to the crystal layer). The first collimator may be constructed of a material that is opaque to gamma photons (e.g., lead and/or tungsten). Further, the first collimator may include at least one aperture that is configured to let incident gamma photons pass along a pre-defined direction of incidence towards the crystal layer. For example, the first detection unit may be configured as a first detection head of the SPECT unit.

In one embodiment, the first gamma camera may be configured to acquire the supervision dataset including a dosimetric mapping of the radiation (e.g., the gamma photons) emitted by the at least one radiation source (e.g., 2D and/or 3D spatially resolved and/or time-resolved). In addition, the at least one gamma camera may be mounted rotatably around an axis of rotation (e.g., around the subject), and thereby be enabled to map the detected gamma photons tomographically.

The aforementioned embodiment of the proposed system may allow a monitoring of the brachytherapy treatment via a direct dosimetric mapping of the radiation emitted by the at least one radiation source.

In an embodiment of the system, the first collimator may be a high-energy and/or pin-hole collimator.

Radiation sources used in brachytherapy treatment (e.g., in HDR and/or PDR brachytherapy treatment) often include Iridium-192 ($^{192}Ir$) radionuclides. The $^{192}Ir$ decay modes may include beta particles and gamma radiation (e.g., gamma photon emission). $^{192}Ir$ may often decay in 95.13% of the time through negative beta emission to $^{192}Pt$. Through electron capture $^{192}Ir$ may decay in about 4.87% of the time to $^{192}Os$. In the process, a gamma photon with an average energy of 380 keV (e.g., maximum 1.06 MeV) may be released in the process. Although $^{192}Ir$ is not commonly used in diagnostic scintigraphy (e.g., SPECT), the energies of gamma photons emitted by an $^{192}Ir$-decay are similar to the energies of gamma photons emitted by an Iodine-131 ($^{131}I$)-decay, which is often used in thyroid cancer therapy, monitored using SPECT. In 89% of the time, $^{131}I$ may decay into stable $^{131}Xe$ by an energy expense of 971 keV decay energy. This decay of $^{131}I$ may include two steps, with gamma decay following rapidly after beta decay. The primary emissions of the $^{131}I$ decay may thus be electrons with a maximal energy of 606 keV (e.g., 89% abundance, others 248 to 807 keV) and 364 keV gamma photons (e.g., 81% abundance, others 723 keV). While other radionuclides used in diagnostic scintigraphy (e.g., $^{131}I$) typically exhibit a radioactivity of a few hundreds of MBq, $^{192}Ir$ can exhibit radioactivity of the order of 10 GBq (e.g., two orders of magnitude higher than $^{131}I$).

The significantly increased radioactivity may saturate a gamma camera with standard (e.g., diagnostic) settings. By configuring the first collimator as a pin-hole collimator, which features a single pin-hole aperture, the sensitivity of the first gamma camera may be reduced to a level where the very high count rates for the gamma photons emitted by the at least one radiation source may be handled. In order to further achieve a large magnification factor and/or a very high spatial resolution in the mapping of the detected gamma photons, the pin-hole collimator may be configured as an ultra-high-resolution (UHR) pin-hole collimator, featuring an aperture of, for example, about 1 mm.

In addition, the above-mentioned radionuclides used as radiation source in brachytherapy treatment emit high-energy gamma photons (e.g., at 100 keV or above). As a consequence, the material of the first collimator may at least partially be penetrated by gamma photons emitted by the at least one radiation source. Disadvantageously, this may lead to an increased saturation of the first gamma camera and/or dosimetry artefacts. By further configuring the first collimator as a high-energy (HE) collimator, such unwanted effects may be avoided. The high-energy collimator may feature a comparably thicker and/or more dense radio-opaque material, thereby limiting the portion of gamma photons transmitted to the crystal layer to the aperture.

In one embodiment, the first collimator may be configured as a high-energy and ultra-high-resolution (HEUHR) pin-hole collimator. In one embodiment, the support structure and/or the rotating gantry frame, to which the first detection unit is rotatably mounted to, may be reinforced in order to bear an increased weight of the first detection unit caused by the first collimator.

The aforementioned embodiment of the system may permit a high-resolution mapping of high-energy gamma photons emitted by the at least one radiation source.

In an embodiment of the system, the SPECT unit may further include a second detection unit. Further, the second detection unit may include a second gamma camera and a second collimator. In one embodiment, the second collimator may be spatially arranged within a field of view of the second gamma camera. The second collimator may be configured to collimate incident gamma photons towards the second gamma camera. In addition, the second gamma camera may be configured to detect gamma photons emitted by the at least one radiation source. Further, a main mapping direction of the first detection unit may be substantially not collinear with a main mapping direction of second detection unit. Further, the SPECT unit may be configured to acquire the supervision dataset by mapping the gamma photons detected by the first and second gamma camera in 3D.

The second detection unit (e.g., the second gamma camera and the second collimator) may include, for example, all properties and/or features that have been described with regard to the first detection unit (e.g., the first gamma camera and the first collimator, respectively).

The main mapping direction of the first detection unit may denote a spatial direction (e.g., a central spatial direction) of gamma photon incidence detectable by the first gamma camera. For example, the main mapping direction of the first detection unit may be a normal to a mapping plane of the first gamma camera. If the first collimator is configured as a pin-hole collimator, the main mapping direction of the first detection unit may further run through the pin-hole aperture of the first collimator. Likewise, the main mapping direction of the second detection unit may denote a spatial direction (e.g., central spatial direction) of gamma photon incidence detectable by the second gamma camera. For example, the main mapping direction of the second detection unit may be a normal to a mapping plane of the second gamma camera. If the second collimator is configured as a pin-hole collimator, the main mapping direction of the second detection unit may further run through the pin-hole aperture of the second collimator.

In one embodiment, the first detection unit and the second detection unit may be spatially arranged such that the respective main mapping directions are substantially not collinear. Further, the first detection unit and the second detection unit may be mounted rotatably around a common axis of rotation. For example, the second detection unit may be configured as a second detection head of the SPECT unit. Further, the first detection unit and the second detection unit may have a common center of rotation (e.g., a common isocenter). The main mapping direction of the first detection unit and the main mapping direction of the second detection unit may intersect (e.g., at the common isocenter) at an angle of intersection. For example, the first detection unit and the second detection unit may be spatially arranged such that the angle of intersection substantially amounts to 90 degrees. In one embodiment, SPECT unit may be configured to acquire the supervision dataset by rotating first and second detection unit in a spatial arrangement around the common axis of rotation and/or the common isocenter, where the angle of intersection remains constant. Hence, the gamma photons emitted by the at least one radiation source may be detected by the first detection unit and the second detection unit (e.g., the first gamma camera and the second gamma camera) from different spatial directions (e.g., angulations). Thereby, a biplanar mapping of the gamma photons emitted by the at least one radiation source may be enabled.

In an embodiment of the system, the second collimator may be a high-energy and/or pin-hole collimator.

All features and advantages laid out above regarding the embodiment of the system where the first collimator is a high-energy and/or a pin-hole collimator also apply to this embodiment. In one embodiment, the first collimator and the second collimator may each be configured as a high-energy and/or pin-hole collimator.

The aforementioned embodiment of the system may permit a high-resolution 3D-mapping of high-energy gamma photons emitted by the at least one radiation source. In one embodiment, the support structure and/or the rotating gantry frame that the second detection unit is rotatably mounted to may be reinforced in order to bear an increased weight of the second detection unit caused by the second collimator.

In an embodiment of the system, the SPECT unit and the CT unit may be arranged in a SPECT/CT-configuration. Further, the CT unit may be configured to acquire the planning dataset. In addition, the supervision dataset may be co-registered with the planning dataset.

The SPECT unit and the CT unit may each be mounted rotatably around a common axis of rotation. Further, the SPECT unit (e.g., the at least one detection unit) and the CT unit (e.g., the X-ray source and the X-ray detector) may be configured to rotate independently around the common axis of rotation. Further, the SPECT unit and the CT unit may respectively be configured to acquire the supervision dataset and the planning dataset substantially coplanar with respect to the common axis of rotation. In one embodiment, the subject may be positioned in a common receiving area of the SPECT unit and the CT unit (e.g., substantially along the common axis of rotation). The CT unit may be configured to acquire the planning dataset (e.g., including pre-procedural image data) of the treatment region. Further, the SPECT unit may be configured to acquire the supervision dataset. Thereby, the supervision dataset may be (e.g., inherently) co-registered with the planning dataset. For example, the supervision dataset and the planning dataset may include a representation of the treatment region in a common coordinate system.

The aforementioned embodiment of the system may provide a more precise supervision of the brachytherapy treatment.

In an embodiment of the system, the SPECT unit and the CT unit may be arranged in a SPECT/CT-configuration. Further, the brachytherapy treatment plan may include at least one planned positioning for the at least one medical guide instrument. In addition, the CT unit may be configured to acquire a first intra-procedural image dataset of the treatment region. In one embodiment, the first intra-procedural image dataset may include a representation of the at least one medical guide instrument. Further, the supervision dataset may be co-registered with the first intra-procedural image dataset. Further, the processing unit may be configured to identify at least one actual positioning of the at least one medical guide instrument in the first intra-procedural image dataset. In addition, the processing unit may further be configured to provide the supervision information additionally based on a comparison between the at least one planned and the at least one actual positioning of the at least one medical guide instrument.

The first intra-procedural image dataset may represent (e.g., map) the treatment region intra-procedurally (e.g., at a time after the at least one medical guide instrument and/or the at least one radiation source have been positioned within the treatment region). In one embodiment, the first intra-procedural image dataset may feature a 2D and/or 3D spatial resolution. In addition, the first intra-procedural image dataset may be time-resolved. The identification of the at least one actual positioning of the at least one medical guide instrument in the first intra-procedural image dataset may include an identification (e.g., a segmentation) of pixels and/or voxels of the first intra-procedural image dataset; the pixels and/or voxels represent the at least one medical guide instrument. For example, the processing unit may be configured to identify the at least one actual positioning of the at least one medical guide instrument based on a contour and/or marker structure of the at least one medical guide instrument represented in the intra-procedural dataset. The marker structure may, for example, be attached and/or integrated and/or inserted to the at least one medical guide instrument. In one embodiment, if intra-procedurally a plurality of medical guide instruments are positioned at least partially within the treatment region, each medical guide instrument may feature a unique marker structure, thereby making the medical guide instruments distinguishable from each other. In one embodiment, the processing unit may be configured to identify each medical guide instrument of the plurality of medical guide instruments based on the unique marker structure. Further, the processing unit may be configured to associate each medical guide instrument, represented in the first intra-procedural image dataset, with a corresponding channel of the afterloader unit to which the medical guide instrument is connected.

Alternatively or in addition, the processing unit may be configured to identify the at least one actual positioning of the at least one medical guide instrument based on a comparison of image values and/or contrast values of the pixels and/or voxels of the first intra-procedural image dataset with a second image value threshold. Further, the processing unit may be configured to identify the at least one actual positioning with respect to the coordinate system of the medical imaging system and/or the coordinate system of the subject. The at least one planned positioning may include at least one planned position and/or orientation for the at least one medical guide instrument. Likewise, the at least one actual positioning may include at least one actual position and/or orientation of the at least one medical guide instrument.

In one embodiment, the supervision dataset may be (e.g., inherently) co-registered with the first intra-procedural image dataset. For example, the supervision dataset and the planning dataset may include a representation of the treatment region in a common coordinate system.

Further, the processing unit may be configured to compare the at least one planned positioning with the at least one actual positioning of the at least one medical guide instrument. Further, the processing unit may be configured to provide the supervision information additionally based on this comparison (e.g., based on an identified deviation between the at least one planned positioning and the at least one actual positioning). Thereby, the system may be configured to validate a correct positioning of the medical guide instruments for the delivery of the brachytherapy treatment. For example, the system may be configured to account for subject motion and/or organ filling, which may have occurred between a time of the acquisition of the planning dataset and a time of the acquisition of the first intra-procedural image dataset.

In an embodiment of the system, the CT unit may be configured to acquire the supervision dataset including a second intra-procedural image dataset of the treatment region. Further, the second intra-procedural image dataset may include the time-resolved intra-procedural representation of the at least one radiation source. Further, the processing unit may further be configured to determine the at least one actual dwell position and the at least one actual dwell time based on the second intra-procedural image dataset.

The second intra-procedural image dataset may represent (e.g., map) the treatment region intra-procedurally (e.g., at a time after the at least one radiation source has been positioned within the treatment region). For example, the second intra-procedural image dataset may map the at least one radiation source as a saturated and/or bright region within the representation of the treatment region. The pixels and/or voxels representing the at least one radiation source may be identified by comparing their values (e.g., an intensity and/or absorption and/or attenuation and/or contrast value) with the first image value threshold. The processing unit may further be configured to associate each pixel and/or voxel of the supervision dataset (e.g., the second intra-procedural image dataset) with a spatial position (e.g., in the coordinate system of the subject). Thereby, the processing unit may be configured to determine the at least one actual dwell position and at least one actual dwell time of the at least one radiation source based on the second intra-procedural image dataset.

The aforementioned embodiment may enable a real-time monitoring of the radiation dose delivered by the at least one radiation source (e.g., without a direct dosimetric mapping). In one embodiment, the determination of the actual dose distribution may include a combination (e.g., a multiplication and/or integration and/or convolution) of the at least one actual dwell position, the at least one actual dwell time, and a radioactivity parameter of the at least one radiation source.

In an embodiment of the system, the processing unit may be further configured to determine a deviation between the planned and actual dose distribution. In addition, the processing unit may be configured to compare the deviation with a pre-defined threshold. Further, the processing unit may be configured to adapt and/or redefine the brachytherapy treatment plan based on the supervision information and/or the supervision dataset in case the deviation reaches and/or exceeds the pre-defined threshold.

The processing unit may be configured to determine the deviation between the actual dose distribution and the planned dose distribution via calculating a difference and/or ratio between the actual dose distribution and the planned dose distribution. Further, the processing unit may be configured to determine the deviation spatially resolved and/or time-resolved. Further, the processing unit may be configured to determine the deviation via comparing the at least one planned with the at least one actual dwell position and the at least one planned with the at least one actual dwell time. Specifically, the processing unit may be configured to determine a deviation measure and/or a deviation map (e.g., globar and/or local) based on the comparison between the planned and actual dose distribution.

The pre-defined threshold may include an upper limit for a deviation in radiation dose and/or dwell time and/or dwell position. The processing unit may be configured to receive and/or determine the pre-defined threshold (e.g., based on a user input and/or the planning dataset and/or the brachytherapy treatment plan). The processing unit may be configured to compare the deviation (e.g., the deviation measure and/or the deviation map) with the pre-defined threshold. Further, the processing unit may be configured to adapt and/or redefine the brachytherapy treatment plan based on the supervision information and/or the supervision dataset in case the deviation reaches and/or exceeds the pre-defined threshold. For example, the processing unit may be configured to adapt and/or redefine the brachytherapy treatment plan taking into account the radiation dose already delivered to the treatment region via the at least one radiation source. The adaption and/or redefinition of the brachytherapy treatment plan may include an alteration and/or dismissal of already planned dwell positions and/or dwell times of the at least one radiation source. Alternatively or in addition, the adaption and/or redefinition of the brachytherapy treatment plan may include an addition of newly planned dwell positions and/or dwell times.

The processing unit may further be configured to provide the adapted and/or redefined brachytherapy treatment plan. The providing of the adapted and/or redefined brachytherapy treatment plan may include a storing on an electronically readable storage medium and/or a displaying on a display unit and/or transmitting to the afterloader unit.

In an embodiment of the system, the system may further include an afterloader unit. The afterloader unit may be communicatively coupled to the processing unit. In addition, the processing unit may be configured to provide the adapted and/or redefined brachytherapy treatment plan to the afterloader unit. Further, the at least one medical guide instrument may be connected (e.g., detachably connected) to the afterloader unit. The afterloader unit may be configured to reposition the at least one radiation source along the at least one medical guide instrument in accordance with the adapted and/or redefined brachytherapy treatment plan.

The afterloader unit may include at least one channel (e.g., a connecting interface) that may be configured to connect (e.g., couple) at least one medical guide instrument. In addition, the afterloader unit may be configured to introduce and/or translate a carrier instrument inside the at least one medical guide instrument. The carrier instrument may be configured to encapsule and/or carry the at least one radiation source (e.g., as a wire). In addition, the carrier instrument may be configured to be inserted into and translated along the elongated hollow lumen of the at least one medical guide instrument. The afterloader unit may include a, for example, electromagnetic and/or mechanical and/or pneumatic stepping motor that is configured to introduce and/or translate the carrier instrument (e.g., the at least one radiation source) inside the at least one medical guide instrument. In addition, the afterloader unit (e.g., the stepping motor) may be configured to extract the carrier instrument (e.g., the at least one radiation source) from the at least one medical guide instrument. In addition, the afterloader unit may include multiple channels, where the afterloader unit may be configured to introduce and/or translate the at least one radiation source inside the at least one medical guide instruments through these channels (e.g., simultaneously or sequentially).

The afterloader unit may further include a communication interface that is configured to communicate (e.g., bi-directionally) with the processing unit. Further, the afterloader unit (e.g., the communication interface) may be configured to receive the adapted and/or redefined brachytherapy treatment plan.

The afterloader unit (e.g., the stepping motor) may be configured to reposition the carrier instrument (e.g., the at least one radiation source) along the at least one medical guide instrument in accordance with the adapted and/or redefined brachytherapy treatment plan. The repositioning of the carrier instrument (e.g., the at least one radiation source) may include an insertion and/or translation and/or extraction with regard to the at least one medical guide instrument.

The aforementioned embodiment of the system may enable a feedback loop (e.g., real-time feedback loop) between the medical imaging system and the afterloader unit via the processing unit. Thereby, the afterloader unit may control the positioning of the at least one radiation source in accordance with the adapted and/or redefined brachytherapy treatment plan, which can prevent radiation damage to the subject.

In a second aspect, the present embodiments include a method for providing a supervision information. A planning dataset including a pre-procedural representation of a treatment region of a subject is received. Further, a brachytherapy treatment plan is determined based on the planning dataset. The brachytherapy treatment plan includes a planned dose distribution for at least one radiation source to be positioned within the treatment region. In addition, a supervision dataset is acquired by a medical imaging system, where the medical imaging system includes a SPECT unit and/or a CT unit. Further, the supervision dataset includes an intra-procedural representation of the at least one radiation source that has been positioned at a treatment site within the treatment region via at least one medical guide instrument before the beginning of this method. Further, the supervision dataset and the planning dataset are being registered. Subsequently, an actual dose distribution is determined based on the supervision dataset. Hereinafter, the supervision information may be provided based on a comparison between the planned and actual dose distribution.

All remarks and advantages laid out above regarding the system for supporting a brachytherapy treatment also apply to the method for providing a supervision information according to the present embodiments and vice versa. Additional acts or sub-acts may be added regarding additional units according to the described embodiments of the system, which may also be transferred to advantageous embodiments of the method for providing a supervision information and vice versa.

In an embodiment of the method, the brachytherapy treatment plan may include at least one planned dwell position and at least one planned dwell time for the at least one radiation source to be positioned. Further, the intra-procedural representation of the at least one radiation source may be time-resolved. In addition, at least one actual dwell position and at least one actual dwell time of the at least one radiation source may be determined based on the supervision dataset. Further, the comparison between the planned dose distribution and actual dose distribution may include a comparison between the at least one planned dwell position and the at least one actual dwell position and between the at least one planned dwell time and the at least one actual dwell time.

In an embodiment of the method, the SPECT unit and the CT unit may be arranged in a SPECT/CT-configuration. In addition, the supervision dataset may be acquired by the SPECT unit through a mapping of gamma photons emitted by the at least one radiation source. In addition, the planning dataset may be acquired by the CT unit. In one embodiment, the supervision dataset may be co-registered with the planning dataset.

In an embodiment of the method, the SPECT unit and the CT unit may be arranged in a SPECT/CT-configuration. Further, the brachytherapy treatment plan may further include at least one planned positioning for the at least one medical guide instrument. In addition, the supervision dataset may be acquired by the SPECT unit through a mapping of gamma photons emitted by the at least one radiation source. In addition, a first intra-procedural image dataset of the treatment region may be acquired by the CT unit. In one embodiment, the first intra-procedural image dataset may include a representation of the at least one medical guide instrument. Further, the supervision dataset may be co-registered with the first intra-procedural image-dataset. Further, at least one actual positioning of the at least one medical guide instrument may be identified in the first intra-procedural image dataset. Further, the providing of the supervision information may be also based on a comparison between the at least one planned positioning of the at least one medical guide instrument and the at least one actual positioning of the at least one medical guide instrument.

In an embodiment of the method, the supervision dataset may be acquired by the CT unit. The supervision dataset includes a second intra-procedural image dataset. In one embodiment, the second intra-procedural image dataset may include the time-resolved intra-procedural representation of the at least one radiation source. In addition, the at least one actual dwell position and the at least one actual dwell time may be determined based on the second intra-procedural image dataset.

In an embodiment of the method, the comparison between the planned dose distribution and the actual dose distribution may include determining a deviation between the planned dose distribution and the actual dose distribution. The deviation is compared with a pre-defined threshold. The brachytherapy treatment plan is adapted and/or redefined based on the supervision information and/or the supervision dataset if the deviation reaches and/or exceeds the pre-defined threshold.

In a third aspect, the present embodiments include a computer program product. The computer program product may include a computer program. The computer program according to the present embodiments may, for example, be directly loaded into a memory of a processing unit (e.g., a control device of a medical imaging system) and includes program means to perform the acts of a method according to the present embodiments if the computer program is executed in the processing unit. The computer program may be stored on an electronically readably storage medium, which thus includes electronically readable control information stored thereon. The control information includes at least a computer program according to the present embodiments and is configured such that the control information executes a method according to the present embodiments when the storage medium is used in a processing unit (e.g., a control device of a medical imaging system). The electronically readably storage medium according to the present embodiments may be a non-transient medium (e.g., a CD-ROM). The computer program product may include further elements, such as a documentation and/or additional components (e.g., hardware dongles for using the software).

In addition, the present embodiments may also emanate from an electronically readable storage medium that stores electronically readable control information such that the control information executes a method according to the present embodiments when the storage medium is used in a processing unit.

A largely software-based implementation bears the advantage that previously used processing units may be easily upgraded via a software update in order to execute a method according to the present embodiments.

DETAILED DESCRIPTION

Figure 1:
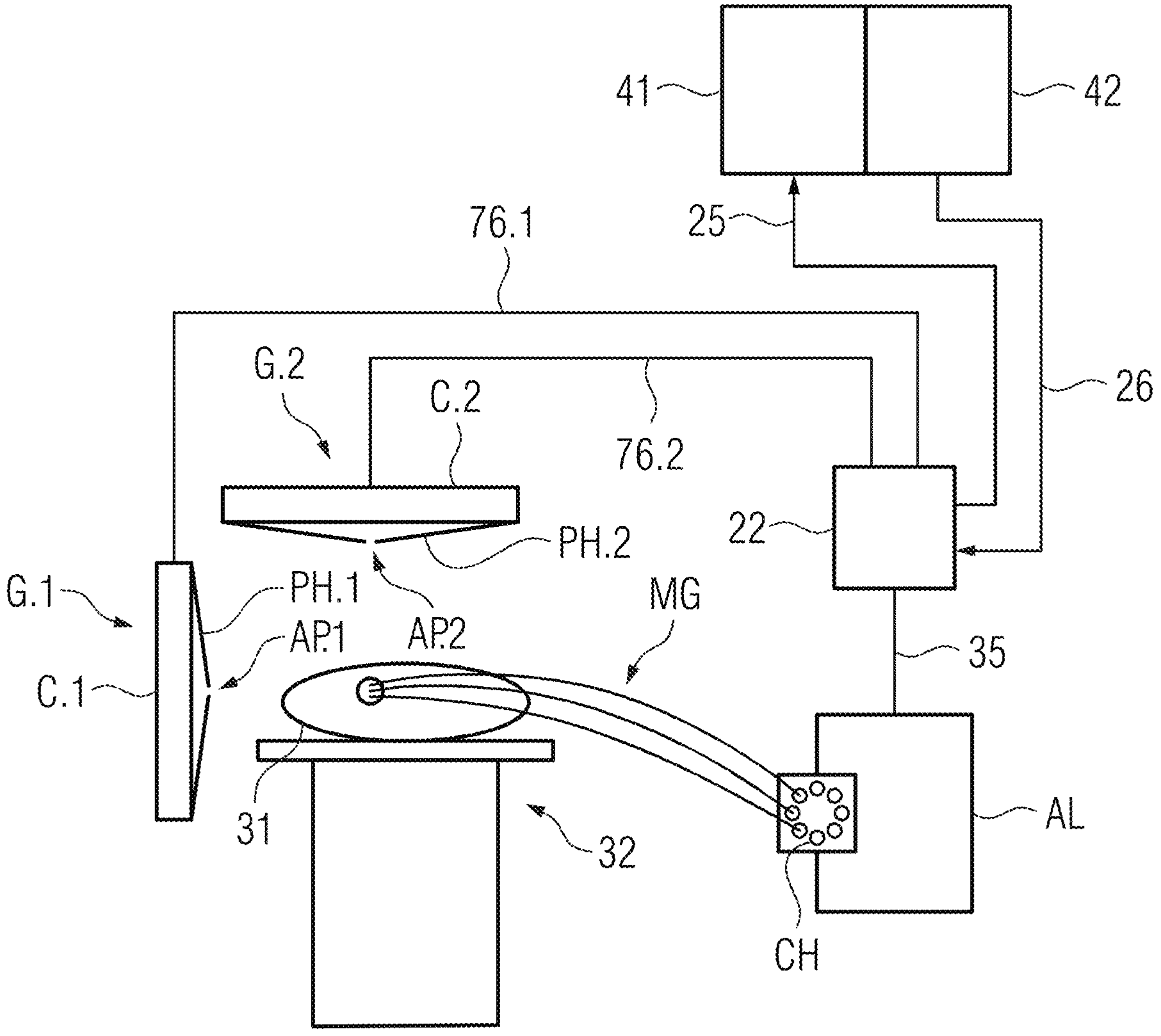
FIG. 1 shows a schematic representation of an embodiments of a system for supporting a brachytherapy.

FIG. 1 shows a schematic representation of an embodiment of a system for supporting a brachytherapy treatment. The system may include a medical imaging system and a processing unit 22. For example, the medical imaging system may include a SPECT unit. The processing unit 22 may be configured to receive a planning dataset comprising a pre-procedural representation of a treatment region of a subject 31. Further, the processing unit 22 may be configured to determine a brachytherapy treatment plan based on the planning dataset, where the brachytherapy treatment plan includes a planned dose distribution for at least one radiation source to be positioned within the treatment region.

The SPECT unit may include a first detection unit G.1 and a second detection unit G.2. The first detection unit G.1 may include a first gamma camera C.1 and a first collimator PH.1. In addition, the second detection unit G.2 may include a second gamma camera C.2 and a second collimator PH.2. In one embodiment, the first collimator PH.1 and the second collimator PH.2 may each be a high-energy and/or pin-hole collimator, featuring a pin-hole aperture AP.1, AP.2. The first collimator PH.1 may be spatially arranged within a field of view of the first gamma camera C.1. Likewise, the second collimator PH.2 may be spatially arranged within a field of view of the second gamma camera C.2. The first PH.1 and second collimator PH.1 may each be configured to collimate incident gamma photons towards the first gamma camera C.1 and the second gamma camera C.2, respectively. Further, the first gamma camera C.1 and the second gamma camera C.2 may each be configured to detect gamma photons emitted by the at least one radiation source. In one embodiment, a main mapping direction of the first detection unit G.1 may be substantially non-collinear with a main mapping direction of the second detection unit G.2. Further, the first detection unit G.1 and the second detection unit G.2 may each provide a signal 76.1 and 76.2 that is dependent on the detected gamma photons to the processing unit 22. Thereby, the SPECT unit may be configured to acquire and to provide a supervision dataset comprising an intra-procedural representation of the at least one radiation source that has been positioned at a treatment site within the treatment region via at least one medical guide instrument MG. The processing unit 22 may be configured to receive the supervision dataset via the signals 76.1 and 76.2. The processing unit 22 may further be configured to register the supervision dataset and the planning dataset. In addition, the processing unit 22 may be configured to determine an actual dose distribution based on the supervision dataset. Moreover, the processing unit 22 may be configured to provide a supervision information based on a comparison between the planned and actual dose distribution.

For example, the processing unit 22 may be configured to determine a deviation between the planned and actual dose distribution. In addition, the processing unit 22 may be configured to compare the deviation with a pre-defined threshold and to adapt and/or redefine the brachytherapy treatment plan based on the supervision information and/or the supervision dataset in case the deviation reaches and/or exceeds the pre-defined threshold.

Further, the system may include an afterloader unit AL. The afterloader unit AL may be communicatively coupled to the processing unit 22 (e.g., via a signal 35). Further, the processing unit 22 may be configured to provide the adapted and/or redefined brachytherapy treatment plan to the afterloader unit AL (e.g., via the signal 35). Further, the at least one medical guide instrument MG may be connected to the afterloader unit AL (e.g., via a channel CH). The afterloader unit AL may be configured to reposition the at least one radiation source along the at least one medical guide instrument MG in accordance with the adapted and/or redefined brachytherapy treatment plan.

The system may further include a display unit 41 (e.g., a display and/or monitor) and/or an input unit 42 (e.g., a keyboard). The input unit 42 may be integrated into the display unit 41 (e.g., as a capacitive and/or resistive touch display). The input unit 42 may be configured to capture a user input (e.g., from medical staff). Further, the processing unit 22 may be configured to receive the user input from the input unit 42 via a signal 26. In addition, the display unit 41 may be configured to display information and/or graphical representations of information (e.g., information and/or parameters of the system and/or components of the system). For this purpose, the processing unit 22 may further be configured to send a signal 25 to the display unit 41. For example, the display unit 41 may be configured to display a graphical representation of the planning dataset, an intra-procedural image dataset, the supervision dataset, and/or the supervision information. Further, the display unit 41 may be configured to display multiple of the aforementioned graphical representations simultaneously (e.g., side-by-side and/or picture-in-picture and/or at least partially overlaid).

Figure 2:
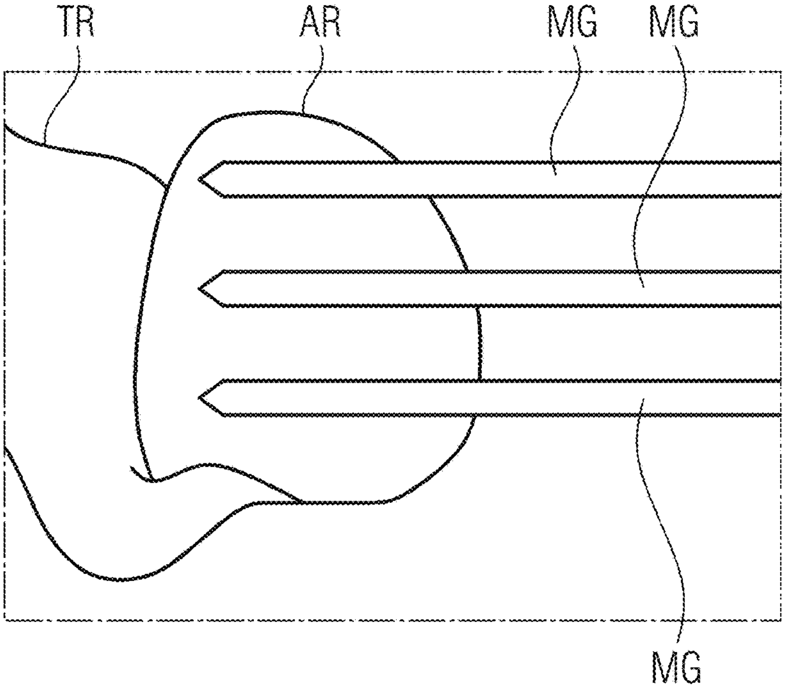
FIGS. 2 and 3 show schematic representations of a treatment region.

FIG. 2 shows a schematic representation of the treatment region TR in a first operating state of the proposed system (e.g., before the at least one radiation source has been positioned within the treatment region TR). The treatment region TR may include an anatomical region AR (e.g., a prostate). Further, a distal portion of the at least one medical guide instrument MG (e.g., three medical guide instruments MG) may be positioned at least partially within and/or adjacent to the treatment region TR (e.g., the anatomical region AR). By way of example, the medical guide instruments MG may be configured as interstitial needles.

Figure 3:
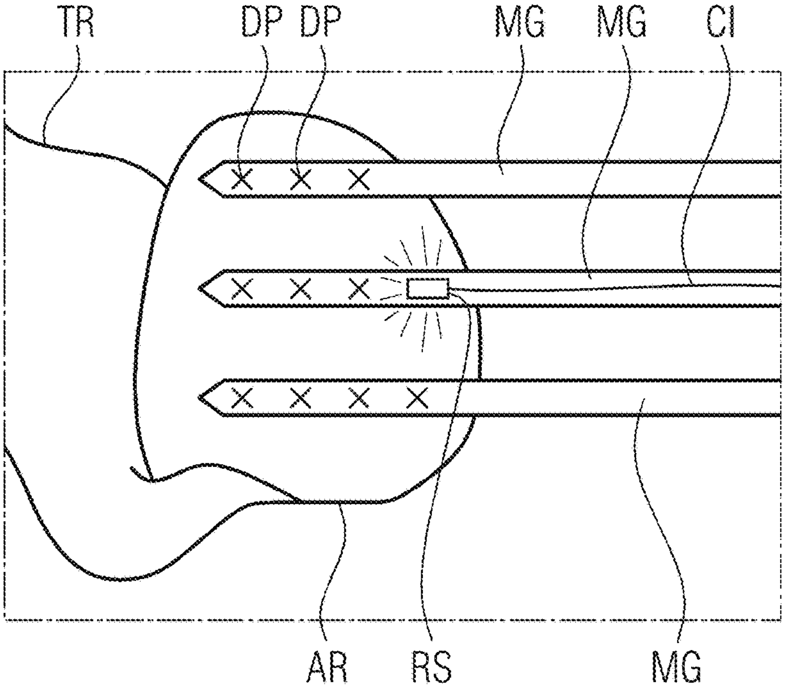

FIG. 3 shows a schematic representation of the treatment region TR in a second operating state of the proposed system (e.g., after the at least one radiation source RS has been positioned within the treatment region TR). In one embodiment, the afterloader unit AL may be configured to introduce and/or translate a carrier instrument CI inside the at least one medical guide instrument MG. The carrier instrument CI may be configured to encapsule and/or carry the at least one radiation source RS (e.g., as a wire). In addition, the carrier instrument CI may be configured to be inserted into and translated along the elongated hollow lumen of the at least one medical guide instrument MG. The afterloader unit AL may include, for example, an electromagnetic and/or mechanical and/or pneumatic stepping motor that is configured to introduce and/or translate the carrier instrument CI (e.g., the at least one radiation source RS) inside the at least one medical guide instrument MG. In addition, the afterloader unit AL (e.g., the stepping motor) may be configured to extract the at carrier instrument CI (e.g., the at least one radiation source RS) from the at least one medical guide instrument MG. In addition, the afterloader unit AL may be configured to introduce and/or translate the at least one radiation source RS inside the at least one medical guide instruments MG through the channels CH (e.g., simultaneously or subsequently).

Further, the afterloader unit AL (e.g., the stepping motor) may be configured to position the carrier instrument CI (e.g., the at least one radiation source RS) along the at least one medical guide instrument MG in accordance with the brachytherapy treatment plan.

In one embodiment, the brachytherapy treatment plan may include at least one planned dwell position DP and at least one planned dwell time for the at least one radiation source RS to be positioned. Further, the intra-procedural representation of the at least one radiation source RS may be time-resolved. Further, the processing unit 22 may be configured to determine at least one actual dwell position and at least one actual dwell time of the at least one radiation source RS based on the supervision dataset. Further, the comparison between the planned and actual dose distribution may include a comparison between the at least one planned DP and the at least one actual dwell position and between the at least one planned and the at least one actual dwell time.

Alternatively or in addition, the brachytherapy treatment plan may include at least one planned positioning for the medical guide instrument MG.

Figure 4:
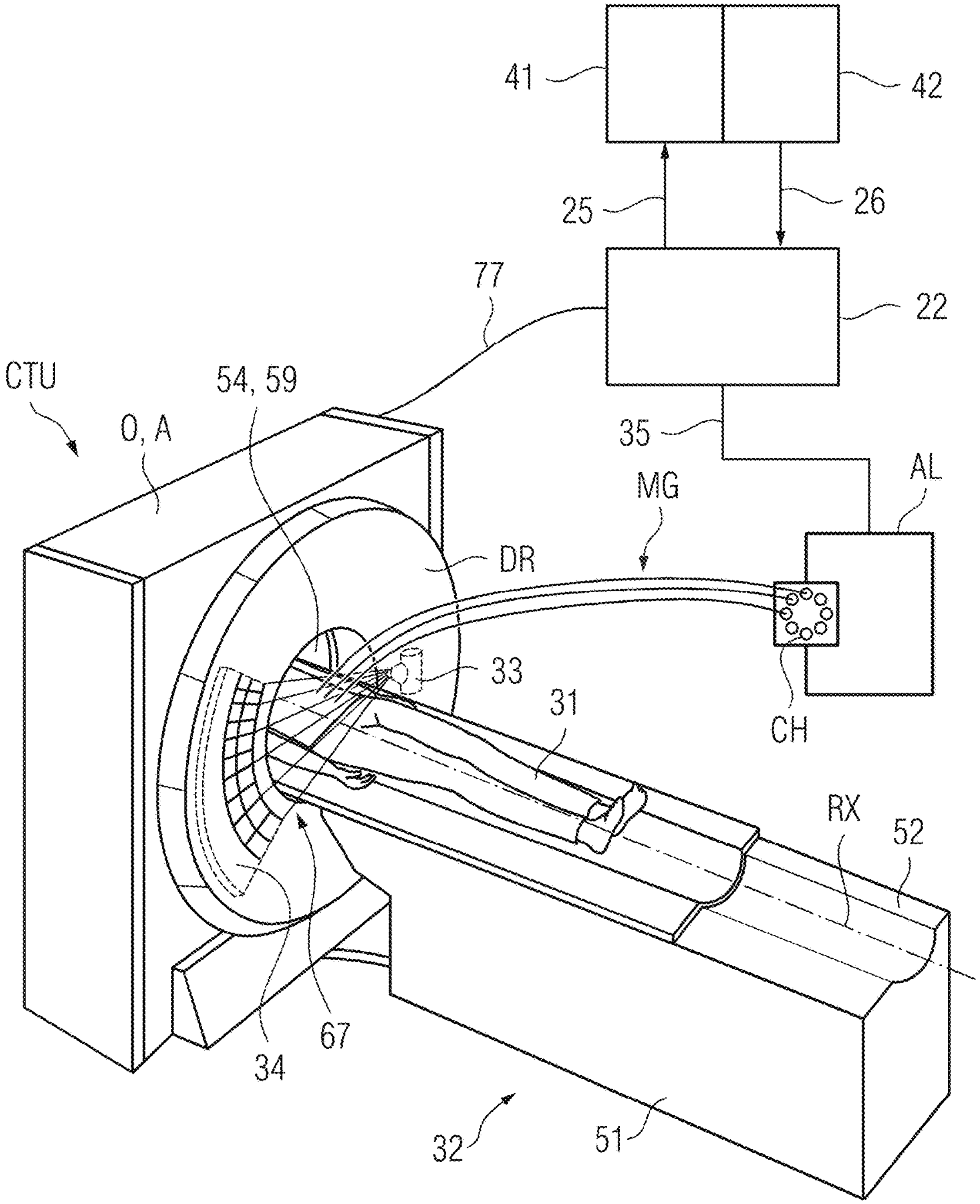
FIGS. 4 and 5 show schematic representations of further embodiments of a system for supporting a brachytherapy.

FIG. 4 shows a schematic representation of a further embodiment of a system. CT unit CTU may include an X-ray source 33, an X-ray detector 34, a cover A, a rotating gantry frame DR, and a rotational bearing (not shown here). The rotating gantry frame DR and the rotational bearing may be covered by the cover A. The X-ray source 33 and the X-ray detector 34 may be mounted on the rotating gantry frame DR opposite each other in relation to an axis of rotation RX. The rotating gantry frame DR may further be mounted rotatably around the axis of rotation RX with respect to the annular frame 0 using the rotational bearing. The subject 31 may be positioned at least partially inside the patient receiving area 59. An acquisition area 54 of the CT unit CTU may be coincident within the patient receiving area 59. The subject 31 (e.g., the treatment area) may be positioned at least partially within the acquisition area 54, such that an X-ray bundle 67 (e.g., a fan-beam) emitted by the X-ray source 33 may be received by the X-ray detector 34 after an interaction between the X-ray bundle and the subject.

The system may further include a patient positioning unit 32, where the patient positioning unit 32 may further include a bearing socket 51 and a bearing plate 52 configured to receive the subject 31. In addition, the bearing plate 52 may be maneuverable with respect to the bearing socket 51 (e.g., such that the bearing plate 52 may be maneuvered along a longitudinal direction of the bearing plate 52 into the acquisition area 54).

The CT unit CTU may be configured to acquire the supervision dataset including a second intra-procedural image dataset of the treatment region TR. Further, the second intra-procedural image dataset may include the time-resolved intra-procedural representation of the at least one radiation source RS. In one embodiment, the processing unit 22 may be configured to determine the at least one actual dwell position and the at least one actual dwell time based on the second intra-procedural image dataset of the at least one radiation source RS.

Figure 5:
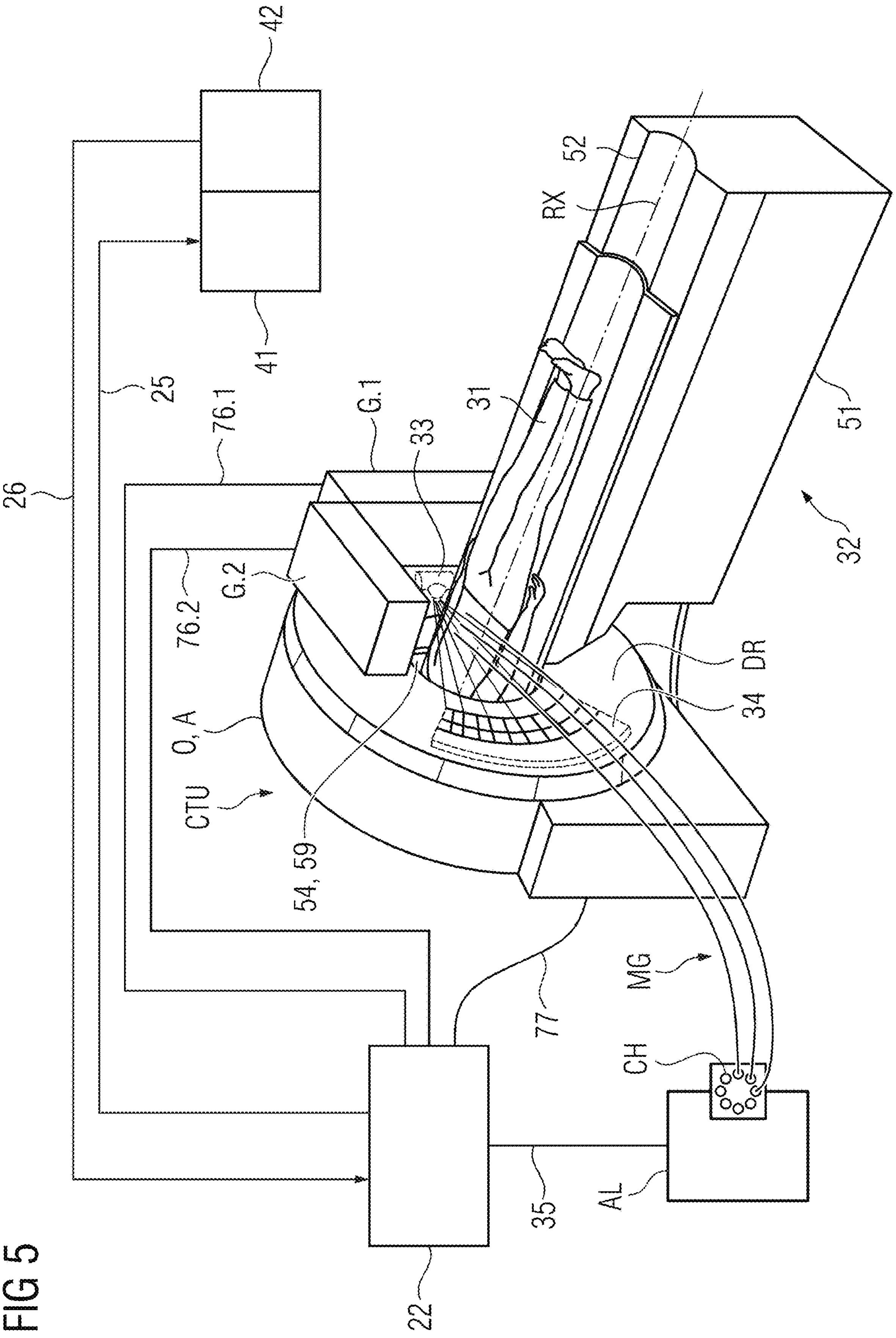

FIG. 5 shows a schematic representation of a further embodiment of a system. The medical imaging system may include a SPECT unit and a CT unit CTU, which are arranged in a SPECT/CT-configuration.

The SPECT unit and the CT unit CTU may each be mounted rotatably around a common axis of rotation RX. For example, the first detection unit G.1 and the second detection unit G.2 may be mounted on the rotating gantry frame DR rotatably around the common axis of rotation RX. In one embodiment, the SPECT unit (e.g., the first detection unit G.1 and the second detection unit G.2) and the CT unit CTU (e.g., the X-ray source 33 and the X-ray detector 34) may be configured to rotate independently around the common axis of rotation RX. In one embodiment, the subject 31 may be positioned in a common receiving area 59 of the SPECT unit and the CT unit CTU (e.g., substantially along the common axis of rotation RX).

The SPECT unit may be configured to acquire the supervision dataset by mapping the gamma photons detected by the first gamma camera C.1 and the second gamma camera C.2 in 3D. Further, the CT unit CTU may be configured to acquire the planning dataset and/or a first intra-procedural image dataset of the treatment region. In one embodiment, the CT unit CTU may be configured to provide the planning dataset and/or the first intra-procedural image dataset via the signal 77 to the processing unit 22. In one embodiment, the supervision dataset may be co-registered with the planning dataset and/or with the first intra-procedural image dataset. For example, the SPECT unit and the CT unit CTU may be configured to simultaneously acquire the supervision dataset and the first intra-procedural image dataset of the treatment region. The first intra-procedural image dataset may include a representation of the at least one medical guide instrument MG. The processing unit 22 may further be configured to identify at least one actual positioning of the at least one medical guide instrument MG in the first intra-procedural image dataset. Further, the processing unit 22 may be configured to provide the supervision information also based on a comparison between the at least one planned positioning and the at least one actual positioning of the at least one medical guide instrument MG, where the brachytherapy treatment plan may include the at least one planned positioning of the at least one medical guide instrument MG.

Further, the SPECT unit and the CT unit CTU may respectively be configured to acquire the supervision dataset and the first intra-procedural image dataset substantially coplanar with respect to the common axis of rotation RX.

Figure 6:
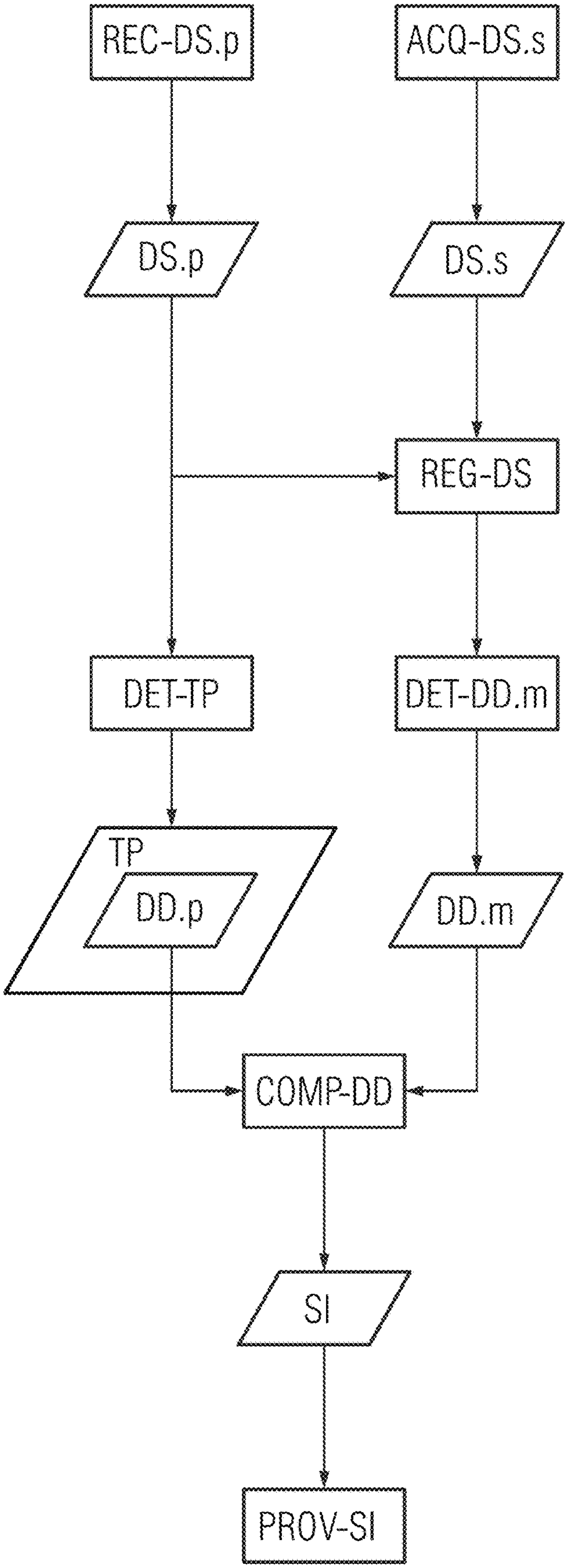
FIGS. 6 to 8 show schematic representations of embodiments of a method for providing a supervision information.

FIG. 6 shows a schematic representation of an embodiment of a method for providing PROV-SI a supervision information SI. In a first act, the planning dataset DS.p including a pre-procedural representation of the treatment region TR of the subject 31 may be received REC-DS.p. Further, the brachytherapy treatment plan TP may be determined DET-TP based on the planning dataset DS.p. The brachytherapy treatment plan TP may include the planned dose distribution DD.p for the at least one radiation source RS to be positioned within the treatment region TR. In a further act, the supervision dataset DS.s may be acquired by the medical imaging system. Further, the supervision dataset DS.s may include the intra-procedural representation of the at least one radiation source RS that has been positioned at the treatment site within the treatment region TR via the at least one medical guide instrument MG before the beginning of this method. Further, the supervision dataset DS.s and the planning dataset DS.p may be registered REG-DS. In addition, the actual dose distribution DD.m may be determined based on the supervision dataset DS.s. Further, the supervision information SI may be provided PROV-SI based on a comparison COMP-DD between the planned DD.p and the actual dose distribution DD.m.

Figure 7:
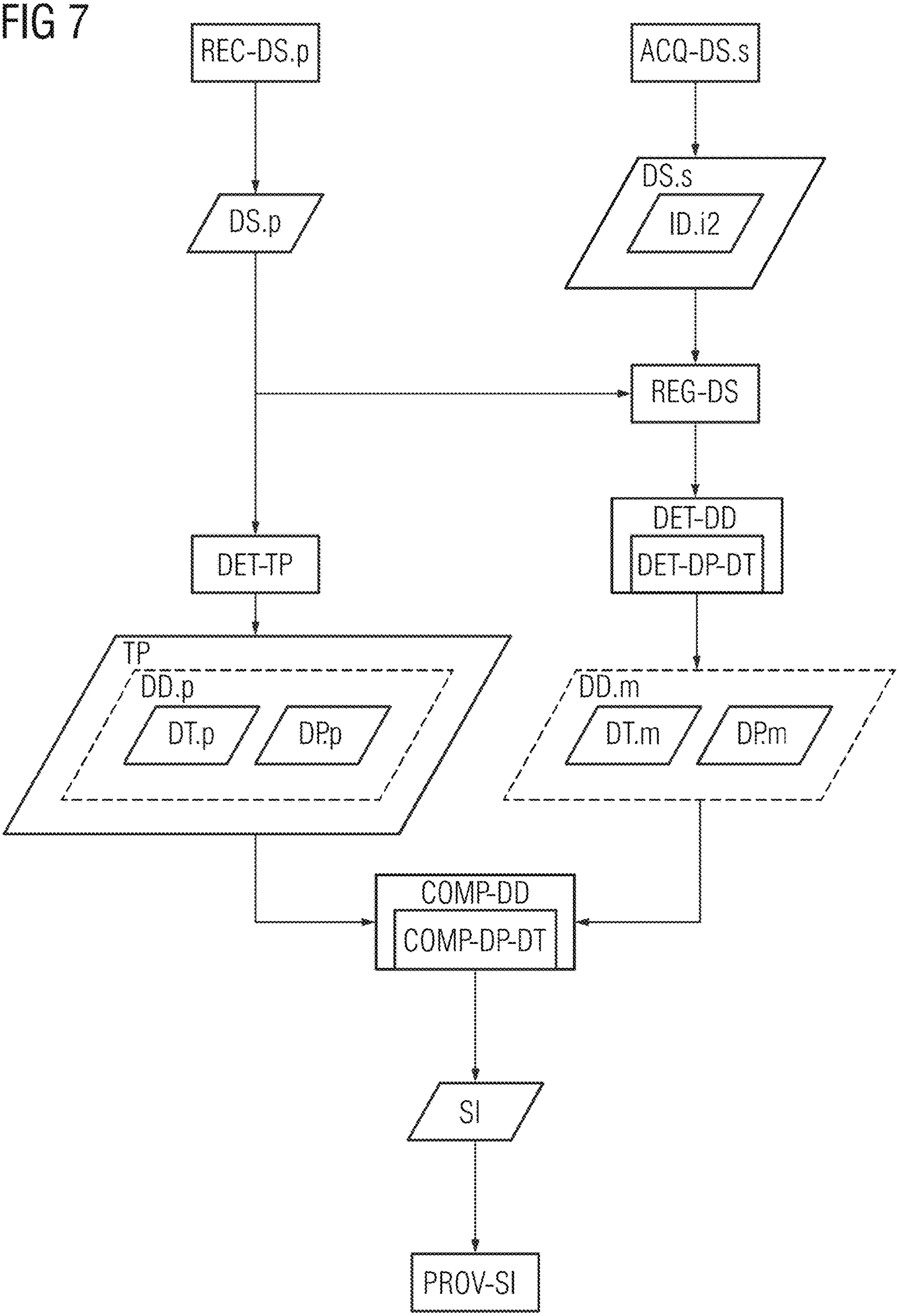

FIG. 7 shows a schematic representation of a further embodiment of a proposed method, where the brachytherapy treatment plan TP may include the at least one planned dwell position DP.p and the at least one planned dwell time DT.p for the at least one radiation source RS to be positioned. Further, the intra-procedural representation of the at least one radiation source RS, which is comprised by the supervision dataset DS.s, may be time-resolved. In addition, the at least one actual dwell position DP.m and the at least one actual dwell time DT.m of the at least one radiation source RS may be determined based on the supervision dataset DS.s. Further, the comparison COMP-DD between the planned dose distribution DD.p and the actual dose distribution DD.m may include a comparison COMP-DP-DT between the at least one planned dwell position DP.p and the at least one actual dwell position DP.m and between the at least one planned dwell time DT.p and the at least one actual dwell time DT.m.

In one embodiment, the supervision dataset DS.s may be acquired ACQ-DS.s by the CT unit CTU including a second intra-procedural image dataset ID.i2, where the second intra-procedural image dataset ID.i2 may include the time-resolved intra-procedural representation of the at least one radiation source RS. Further, the at least one actual dwell position DP.m and the at least one actual dwell time DT.m may be determined based on the second intra-procedural image dataset ID.i2.

Figure 8:
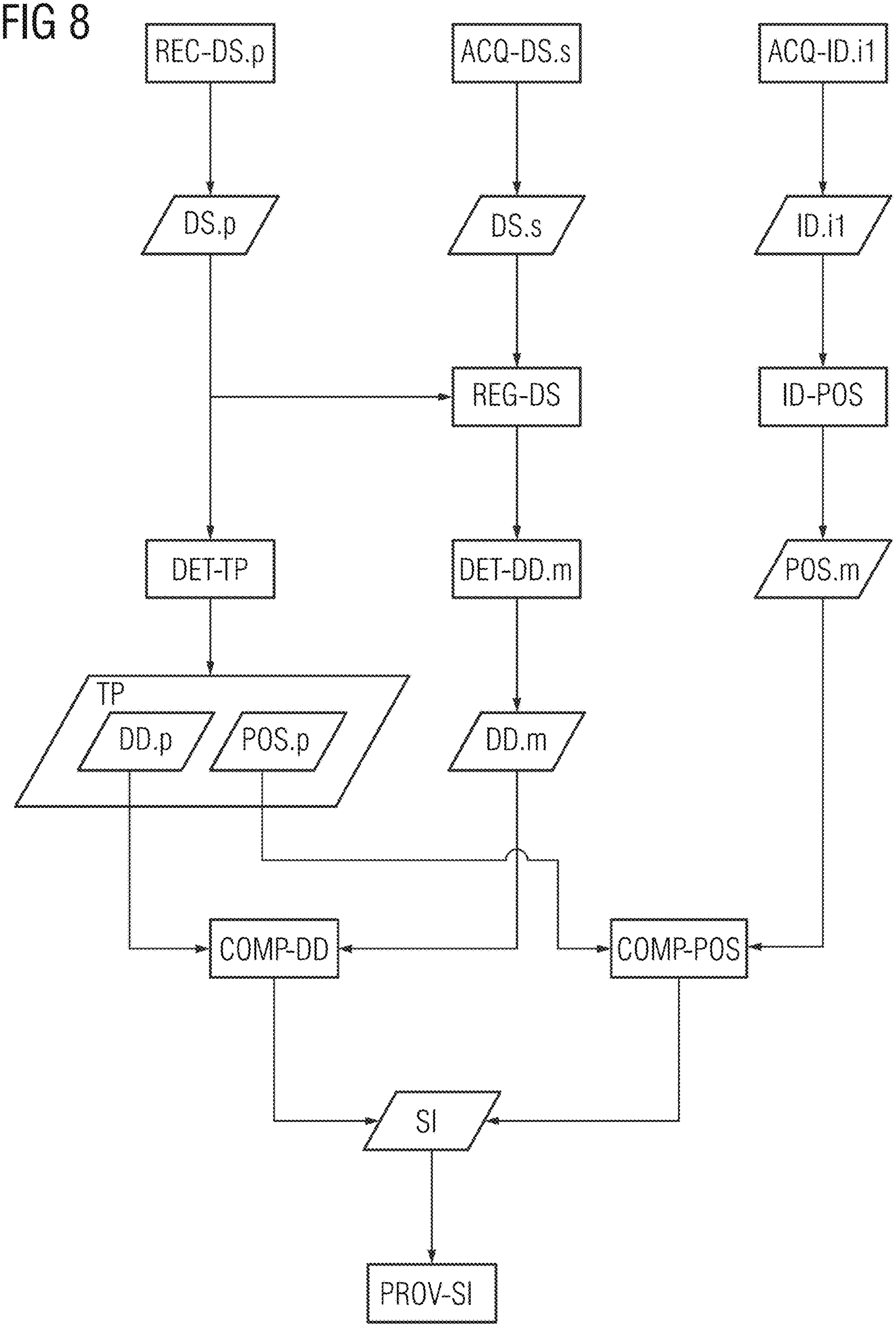

FIG. 8 shows a schematic representation of a further embodiment of a method. The brachytherapy treatment plan TP may further include the at least one planned positioning POS.p for the at least one medical guide instrument MG. In addition, the supervision dataset DS.s may be acquired by the SPECT unit through a mapping of the gamma photons emitted by the at least one radiation source RS. Further, a first intra-procedural image dataset ID.i1 including a representation of the at least one medical guide instrument MG may be acquired ACQ-ID.i1 by the CT unit CTU. In addition, the at least one actual positioning POS.m of the at least one medical guide instrument MG may be identified ID-POS in the first intra-procedural image dataset ID.i1. In one embodiment, the supervision information SI may be provided also based on the comparison COMP-POS between the at least one planned positioning POS.p and the at least one actual positioning POS.m of the at least one medical guide instrument MG.

Although the present invention has been described in detail with reference to exemplary embodiments, the present invention is not limited by the disclosed examples from which the skilled person is able to derive other variations without departing from the scope of the invention. In addition, the utilization of indefinite articles such as “a” and/or “an” does not exclude multiples of the respective features. Further, terms such as “unit” and “element” do not exclude that the respective components may include multiple interacting sub-components, where the sub-components may further be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A system for supporting a brachytherapy treatment, the system comprising:

a medical imaging system; and one or more processors;

wherein the medical imaging system comprises a single photon emission computed tomography (SPECT) unit, a computed tomography (CT) unit, or the SPECT unit and the CT unit, wherein the one or more processors are configured to:

receive a planning dataset comprising a pre-procedural representation of a treatment region of a subject;

determine a brachytherapy treatment plan based on the planning dataset, wherein the brachytherapy treatment plan comprises a planned dose distribution for at least one radiation source to be positioned within the treatment region, wherein the medical imaging system is configured to acquire a supervision dataset, the supervision dataset comprising an intra-procedural representation of the at least one radiation source that, in an operating state of the system, has been positioned at a treatment site within the treatment region via at least one medical guide instrument;

register the supervision dataset and the planning dataset;

determine an actual dose distribution based on the supervision dataset;

provide a supervision information based on a comparison between the planned dose distribution and the actual dose distribution; and control repositioning of the at least one radiation source based on the supervision information or retract the at least one radiation source based on the supervision information.

2. The system of claim 1, wherein the brachytherapy treatment plan comprises at least one planned dwell position and at least one planned dwell time for the at least one radiation source to be positioned, wherein the supervision dataset comprises a time-resolved intra-procedural representation of the at least one radiation source, wherein the one or more processors are further configured to determine at least one actual dwell position and at least one actual dwell time of the at least one radiation source based on the supervision dataset, and wherein the comparison between the planned dose distribution and the actual dose distribution comprises a comparison between the at least one planned dwell position and the at least one actual dwell position and a comparison between the at least one planned dwell time and the at least one actual dwell time.

3. The system of claim 1, wherein the SPECT unit comprises a first detection unit, wherein the first detection unit comprises a first gamma camera and a first collimator, wherein the first collimator is spatially arranged within a field of view of the first gamma camera, wherein the first collimator is configured to collimate incident gamma photons towards the first gamma camera, wherein the first gamma camera is configured to detect gamma photons emitted by the at least one radiation source, and wherein the SPECT unit is configured to acquire the supervision dataset by mapping the detected gamma photons.

4. The system of claim 3, wherein the first collimator is a high-energy collimator, a pin-hole collimator, or a high-energy and pin-hole collimator.

5. The system of claim 3, wherein the SPECT unit further comprises a second detection unit, wherein the second detection unit comprises a second gamma camera and a second collimator, wherein the second collimator is spatially arranged within a field of view of the second gamma camera, wherein the second collimator is configured to collimate incident gamma photons towards the second gamma camera, wherein the second gamma camera is configured to detect gamma photons emitted from the at least one radiation source, wherein a main mapping direction of the first detection unit is substantially not collinear with a main mapping direction of the second detection unit, and wherein the SPECT unit is configured to acquire the supervision dataset by mapping the gamma photons detected by the first gamma camera and the second gamma camera in three dimensions (3D).

6. The system of claim 5, wherein the second collimator is a high-energy collimator, a pin-hole collimator, or a high-energy and pin-hole collimator.

7. The system of claim 3, wherein the SPECT unit and the CT unit are arranged in a SPECT/CT-configuration, wherein the CT unit is configured to acquire the planning dataset, and wherein the supervision dataset is co-registered with the planning dataset.

8. The system of claim 2, wherein the SPECT unit and the CT unit are arranged in a SPECT/CT-configuration, wherein the brachytherapy treatment plan further comprises at least one planned positioning for the at least one medical guide instrument, wherein the CT unit is configured to acquire a first intra-procedural image dataset of the treatment region, wherein the first intra-procedural image dataset comprises a representation of the at least one medical guide instrument, wherein the supervision dataset is co-registered with the first intra-procedural image dataset, and wherein the one or more processors are further configured to:

identify at least one actual positioning of the at least one medical guide instrument in the first intra-procedural image dataset; and provide the supervision information also based on a comparison between the at least one planned positioning and the at least one actual positioning of the at least one medical guide instrument.

9. The system of claim 2, wherein the CT unit is configured to acquire the supervision dataset, the supervision dataset comprising a second intra-procedural image dataset of the treatment region, wherein the second intra-procedural image dataset comprises the time-resolved intra-procedural representation of the at least one radiation source, and wherein the one or more processors are further configured to determine the at least one actual dwell position and the at least one actual dwell time based on the second intra-procedural image dataset.

10. The system of claim 1, wherein the one or more processors are further configured to:

determine a deviation between the planned dose distribution and the actual dose distribution;

compare the deviation with a pre-defined threshold; and adapt, redefine, or adapt and redefine the brachytherapy treatment plan based on the supervision information, the supervision dataset, or the supervision information and the supervision dataset in case the deviation reaches, exceeds, or reaches and exceeds the pre-defined threshold.

11. The system of claim 10, further comprising an afterloader unit that is communicatively coupled to the one or more processors, wherein the one or more processors are further configured to provide the adapted, redefined, or adapted and redefined brachytherapy treatment plan to the afterloader unit, wherein the at least one medical guide instrument is connected to the afterloader unit, and wherein the afterloader unit is configured to reposition the at least one radiation source along the at least one medical guide instrument in accordance with the adapted, redefined, or adapted and redefined brachytherapy treatment plan.

12. A method for providing supervision information, the method comprising:

receiving a planning dataset comprising a pre-procedural representation of a treatment region of a subject;

determining a brachytherapy treatment plan based on the planning dataset, wherein the brachytherapy treatment plan comprises a planned dose distribution for at least one radiation source to be positioned within the treatment region;

acquiring, by a medical imaging system, a supervision dataset, wherein the medical imaging system comprises a single photon emission computed tomography (SPECT) unit, a computed tomography (CT) unit, or the SPECT unit and the CT unit, and wherein the supervision dataset comprises an intra-procedural representation of the at least one radiation source that has been positioned at a treatment site within the treatment region via at least one medical guide instrument before the beginning of the method;

registering the supervision dataset and the planning dataset;

determining an actual dose distribution based on the supervision dataset;

providing the supervision information based on a comparison between the planned dose distribution and the actual dose distribution; and controlling repositioning of the at least one radiation source based on the supervision information or retracting the at least one radiation source based on the supervision information.

13. The method of claim 12, wherein the brachytherapy treatment plan comprises at least one planned dwell position and at least one planned dwell time for the at least one radiation source to be positioned, wherein the supervision dataset comprises a time-resolved intra-procedural representation of the at least one radiation source, wherein the method further comprises determining at least one actual dwell position and at least one actual dwell time of the at least one radiation source based on the supervision dataset, and wherein the comparison between the planned dose distribution and the actual dose distribution comprises a comparison between the at least one planned dwell position and the at least one actual dwell position, and between the at least one planned dwell time and the at least one actual dwell time.

14. The method of claim 12, wherein the SPECT unit and the CT unit are arranged in a SPECT/CT-configuration, wherein the supervision dataset is acquired by the SPECT unit through a mapping of gamma photons emitted by the at least one radiation source, wherein the method further comprises acquiring the planning dataset using the CT unit, and wherein the supervision dataset is co-registered with the planning dataset.

15. The method of claim 12, wherein the SPECT unit and the CT unit are arranged in a SPECT/CT-configuration, wherein the brachytherapy treatment plan further comprises at least one planned positioning for the at least one medical guide instrument, wherein the supervision dataset is acquired by the SPECT unit through a mapping of gamma photons emitted by the at least one radiation source, wherein the method further comprises:

acquiring a first intra-procedural image dataset of the treatment region using the CT unit, wherein the first intra-procedural image dataset comprises a representation of the at least one medical guide instrument; and identifying at least one actual positioning of the at least one medical guide instrument in the first intra-procedural image dataset, and wherein providing the supervision information comprises providing the supervision information also based on a comparison between the at least one planned and the at least one actual positioning of the at least one medical guide instrument.

16. The method of claim 13, further comprising acquiring the supervision dataset comprising a second intra-procedural image dataset using the CT unit, wherein the second intra-procedural image dataset comprises the time-resolved intra-procedural representation of the at least one radiation source, and wherein the at least one actual dwell position and the at least one actual dwell time are determined based on the second intra-procedural image dataset.

17. The method of claim 12, wherein the comparison between the planned dose distribution and the actual dose distribution comprises:

determining a deviation between the planned dose distribution and the actual dose distribution;

comparing the deviation with a pre-defined threshold; and adapting, redefining, or adapting and redefining the brachytherapy treatment plan based on the supervision information, the supervision dataset, or the supervision information and the supervision dataset when the deviation reaches, exceeds, or reaches and exceeds the pre-defined threshold.

18. In a non-transitory computer-readable storage medium that stores instructions executable by one or more processors to provide supervision information, the instructions comprising:

receiving a planning dataset comprising a pre-procedural representation of a treatment region of a subject;

determining a brachytherapy treatment plan based on the planning dataset, wherein the brachytherapy treatment plan comprises a planned dose distribution for at least one radiation source to be positioned within the treatment region;

acquiring, by a medical imaging system, a supervision dataset, wherein the medical imaging system comprises a single photon emission computed tomography (SPECT) unit, a computed tomography (CT) unit, or the SPECT unit and the CT unit, and wherein the supervision dataset comprises an intra-procedural representation of the at least one radiation source that has been positioned at a treatment site within the treatment region via at least one medical guide instrument before the beginning of the provision of the supervision information;

registering the supervision dataset and the planning dataset;

determining an actual dose distribution based on the supervision dataset;

providing the supervision information based on a comparison between the planned dose distribution and the actual dose distribution; and controlling repositioning of the at least one radiation source based on the supervision information or retracting the at least one radiation source based on the supervision information.

* * * * *